United States Patent
Ai et al.

(10) Patent No.: US 11,684,745 B2
(45) Date of Patent: Jun. 27, 2023

(54) VENTILATOR AND GAS SUPPLY CONTROL METHOD THEREOF

(71) Applicant: SHENZHEN MINDRAY BIO-MEDICAL ELECTRONICS CO., LTD., Shenzhen (CN)

(72) Inventors: Shiming Ai, Shenzhen (CN); Gang Yao, Shenzhen (CN); Leping Wu, Shenzhen (CN); Peitao Chen, Shenzhen (CN); Xinsheng Li, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 540 days.

(21) Appl. No.: 16/818,516

(22) Filed: Mar. 13, 2020

(65) Prior Publication Data
US 2020/0206452 A1     Jul. 2, 2020

Related U.S. Application Data

(63) Continuation of application No. PCT/CN2017/101662, filed on Sep. 13, 2017.

(51) Int. Cl.
*A61M 16/12* (2006.01)
*A61M 16/10* (2006.01)
(Continued)

(52) U.S. Cl.
CPC ........ *A61M 16/12* (2013.01); *A61M 16/0066* (2013.01); *A61M 16/107* (2014.02);
(Continued)

(58) Field of Classification Search
CPC .......... A61M 16/0057; A61M 16/0063; A61M 16/0066; A61M 16/01; A61M 16/022;
(Continued)

(56) References Cited

U.S. PATENT DOCUMENTS

| 4,392,514 A | | 7/1983 | Farley et al. |
| 5,237,987 A | * | 8/1993 | Anderson ........... A61M 16/202 |
| | | | 128/204.21 |

(Continued)

FOREIGN PATENT DOCUMENTS

| CN | 201052323 A | 4/2008 |
| CN | 101474451 A | 7/2009 |

(Continued)

OTHER PUBLICATIONS

First Office Action issued in related Chinese Application No. 201780094885.8, dated Jan. 21, 2022, 9 pages.

(Continued)

*Primary Examiner* — Joseph D. Boecker
(74) *Attorney, Agent, or Firm* — Bayes PLLC

(57) ABSTRACT

The present disclosure provides a ventilator that includes a first gas path, comprising a first pressurized gas source adaptor and a first flow adjustment device connected in sequence; a second gas path, comprising a second pressurized gas source adaptor and a second flow adjustment device connected in sequence; a third gas path, comprising a third pressurized gas source adaptor; a first inhalation branch for delivering inhalation gas to a patient; a second inhalation branch for delivering inhalation gas to the patient, including a gas compression device; a switching device, including a first mixing mode connecting the first gas path and the second gas path to the first inhalation branch, and a second mixing mode connecting the first gas path and the third gas path to the second inhalation branch; and an exhalation branch for managing exhaled air of the patient.

11 Claims, 9 Drawing Sheets

(51) Int. Cl.
*A61M 16/20* (2006.01)
*A61M 16/00* (2006.01)

(52) U.S. Cl.
CPC ........ *A61M 16/202* (2014.02); *A61M 16/207* (2014.02); *A61M 16/022* (2017.08); *A61M 16/125* (2014.02); *A61M 2016/0027* (2013.01); *A61M 2016/0033* (2013.01); *A61M 2202/0208* (2013.01)

(58) Field of Classification Search
CPC .......... A61M 16/0883; A61M 16/0891; A61M 16/10; A61M 16/12; A61M 16/125; A61M 16/202; A61M 16/203; A61M 16/204; A61M 16/207; A61M 2016/0027; A61M 2016/0033; A61M 2205/70
See application file for complete search history.

(56) References Cited

U.S. PATENT DOCUMENTS

| | | | |
|---|---|---|---|
| 2007/0125377 A1* | 6/2007 | Heinonen | A61M 16/203 128/204.21 |
| 2008/0121233 A1* | 5/2008 | von Blumenthal | A61M 16/12 128/204.22 |
| 2010/0065056 A1 | 3/2010 | Greter et al. | |
| 2010/0078018 A1* | 4/2010 | Heinonen | A61M 16/01 128/202.22 |
| 2011/0197889 A1* | 8/2011 | Lahde | A61M 16/0833 128/205.12 |
| 2013/0087146 A1 | 4/2013 | Callaghan | |
| 2018/0177961 A1* | 6/2018 | Kagan | A61M 16/0883 |

FOREIGN PATENT DOCUMENTS

| | | |
|---|---|---|
| CN | 102114289 A | 7/2011 |
| CN | 102500026 A | 6/2012 |
| CN | 103055396 A | 4/2013 |
| CN | 203469165 A | 3/2014 |
| CN | 104548296 A | 4/2015 |
| CN | 105963837 A | 9/2016 |
| CN | 106470725 A | 3/2017 |
| CN | 106581833 A | 4/2017 |
| DE | 102014109394 A1 | 1/2016 |
| EP | 1795222 A1 | 6/2007 |
| FR | 2830454 A1 | 4/2003 |
| JP | 2007097931 A | 4/2007 |

OTHER PUBLICATIONS

Extended European Search Report issued in related European Application No. 17925455.2, dated Aug. 17, 2020, 10 pages.
Second Office Action issued in related Chinese Application No. 201710824085.9, dated Jul. 5, 2021, 7 pages.
International Search Report issued in corresponding International Application No. PCT/CN2017/101662, dated Jun. 8, 2018, 4 pages.
Third Office Action issued in related Chinese Application No. 201780094885.8, dated Jan. 31, 2023, 8 pages.

* cited by examiner

VENTILATOR AND GAS SUPPLY CONTROL METHOD THEREOF

CROSS-REFERENCE TO RELATED APPLICATIONS

This application is a by-pass continuation of Patent Cooperation Treaty Application No. PCT/CN2017/101662, filed on Sep. 13, 2017, the content thereof is hereby incorporated by reference in its entirety.

TECHNICAL FIELD

The present disclosure relates to the field of medical instruments, and in particular to a ventilator.

BACKGROUND

Ventilators have been widely used in hospitals as a medical device used to assist patients who have difficulty in respiration or support patients who cannot perform spontaneous respiration to complete mechanical ventilation. Generally, a ventilator requires two gas supply sources including an air source and an oxygen source, and air and oxygen are mixed to supply a mixed gas with a desired oxygen concentration to a patient.

At present, in a hospital equipped with a central gas supply system that can provide an air source, almost all the air of the ventilator is provided by the central gas supply system; and if a hospital lacks a central gas supply system or a central gas supply system has unstable air pressure, an existing ventilator cannot be used in time to provide aid to a patient.

SUMMARY

The present disclosure is provided in view of the foregoing cases, and an objective thereof is to provide a ventilator that does not depend on a central gas supply system and has at least two gas supply modes.

To this end, one aspect of the present disclosure provides a ventilator, including: a first gas path, comprising a first pressurized gas source adaptor and a first flow adjustment device connected in sequence; a second gas path, comprising a second pressurized gas source adaptor and a second flow adjustment device connected in sequence; a third gas path, comprising a third pressurized gas source adaptor; a first inhalation branch for delivering inhalation gas to a patient; a second inhalation branch for delivering inhalation gas to the patient, comprising a gas compression device; a switching device, comprising a first mixing mode connecting the first gas path and the second gas path to the first inhalation branch, and a second mixing mode connecting the first gas path and the third gas path to the second inhalation branch; and an exhalation branch for managing exhaled air of the patient.

In one aspect of the present disclosure, the switching device has a first mixing mode connecting the first gas path and the second gas path to the first inhalation branch, and a second mixing mode connecting the first gas path and the third gas path to the second inhalation branch. The switching device is used to switch between the first mixing mode and the second mixing mode and thus can switch according to a gas supply source and provide a mixed gas with a desired oxygen concentration in time. In addition, the foregoing ventilator can be independent of a central gas supply system.

In addition, in the ventilator in one aspect of the present disclosure, the second gas path further includes: a pressure sensor detecting gas pressure at the second pressurized gas source adaptor; and a controller for controlling the switching device based on a measured value of the pressure sensor, to enable the switching device to switch between the first mixing mode and the second mixing mode. In this way, the controller can determine a pressure value, measured by the pressure sensor, in the second gas path to control the switching device.

In addition, in the ventilator in one aspect of the present disclosure, the switching device may comprise a pilot valve and a pneumatic three-way valve. In this case, the controller may control on or off of the pilot valve and a corresponding action of the pneumatic three-way valve to conveniently implement switching of the switching device between the first mixing mode and the second mixing mode.

In addition, in the ventilator in one aspect of the present disclosure, the second inhalation branch may further comprise a first mixing cavity, and in the second mixing mode, the switching device connects the first gas path and the third gas path to the second inhalation branch by the first mixing cavity. In this case, a gas from the first gas path and a gas from the third gas path can have a better mixing effect in the first mixing cavity, to provide the mixed gas with a desired oxygen concentration.

In addition, in the ventilator in one aspect of the present disclosure, the second inhalation branch may comprise a third flow adjustment device. In this case, because the third flow adjustment device can control the supplied gas, so that a specified amount of inhalation gas can be provided to the patient.

In addition, in the ventilator in one aspect of the present disclosure, the second inhalation branch may further comprise a second mixing cavity, and the second mixing cavity is configured to mix, during inhalation, the mixed gas that is in the second mixing mode and is pressurized by the gas compression device. In this way, a mixing effect of the mixed gas passing through the second mixing cavity can be further improved.

In addition, in the ventilator in one aspect of the present disclosure, the third flow adjustment device may further comprise a flow sensor. In this way, the flow of the mixed gas from the second inhalation branch can be obtained in time.

In addition, in the ventilator in one aspect of the present disclosure, the third flow adjustment device may further comprise a voice coil motor. In this way, the flow of the mixed gas from the second inhalation branch can be obtained in time.

In addition, in the ventilator in one aspect of the present disclosure, the first inhalation branch may further comprise a gas mixing device. In this way, the gas mixing device can be used to thoroughly mix the gas from the first gas path and the gas from the second gas path, thereby improving the mixing effect of the mixed gas.

Another aspect of the present disclosure provides a gas supply control method of a ventilator. The ventilator comprises a first pressurized gas source adaptor, a second pressurized gas source adaptor, a gas compression device, a switching device, and a controller. The switching device has a first mixing mode using the first pressurized gas source adaptor and the second pressurized gas source adaptor for gas supply, and a second mixing mode using the first pressurized gas source adaptor and the gas compression device for gas supply; the controller performs the following operations: when the switching device is in the first mixing mode, detecting a working state of the ventilator and gas pressure at the second pressurized gas source adaptor; determining, according to the detected working state of the ventilator and the detected gas pressure at the second pressurized gas source adaptor, whether the gas pressure at the second pressurized gas source adaptor is adequate; and when the gas pressure at the second pressurized gas source adaptor is inadequate, switching the switching device to the second mixing mode.

In another aspect of the present disclosure, when the switching device is in the first mixing mode, the working state of the ventilator and the gas pressure at the second pressurized gas source adaptor are detected, it is determined according to the detected working state of the ventilator and the detected gas pressure at the second pressurized gas source adaptor whether the gas pressure at the second pressurized gas source adaptor is adequate, and when the gas pressure at the second pressurized gas source adaptor is inadequate, the switching device is switched to the second mixing mode. In this way, it is determined whether gas supply sources work normally, and switching is performed in time according to conditions of the gas supply sources, thereby providing a mixed gas with a desired oxygen concentration.

In addition, in the gas supply control method in another aspect of the present disclosure, the step of determining, according to the detected working state of the ventilator and the detected gas pressure at the second pressurized gas source adaptor, whether the gas pressure at the second pressurized gas source adaptor is adequate specifically comprises: when the ventilator is in a standby state, determining whether the gas pressure at the second pressurized gas source adaptor satisfies a standby pressure threshold and a standby time threshold; if yes, determining that the gas pressure at the second pressurized gas source adaptor is adequate; if not, determining that the gas pressure at the second pressurized gas source adaptor is inadequate; when the ventilator is in the working state, determining whether the gas pressure at the second pressurized gas source adaptor satisfies a first working pressure threshold and a first working time threshold; if not, determining whether the gas pressure at the second pressurized gas source adaptor satisfies a second working pressure threshold and a second working time threshold; if not, determining that the gas pressure at the second pressurized gas source adaptor is inadequate; and if yes, determining that the gas pressure at the second pressurized gas source adaptor is adequate. In this case, when the ventilator is in a standby state or a working state, it is determined whether the gas pressure at a second pressurized gas source satisfies a corresponding condition to determine whether the gas at the second pressurized gas source is adequate.

In addition, in the gas supply control method in another aspect of the present disclosure, the first working pressure threshold is less than the second working pressure threshold, and the first working time threshold is less than the second working time threshold. In this case, it can be determined more effectively whether the gas at the second pressurized gas source adaptor is adequate.

In addition, in the gas supply control method in another aspect of the present disclosure, the gas supply control method further comprises: when the switching device is in the second mixing mode, detecting the working state of the ventilator, and performing gas source test ventilation on the second pressurized gas source adaptor; determining, according to the detected working state and a gas source test ventilation result, whether the gas pressure or a flow rate at the second pressurized gas source adaptor is restored; and if the gas pressure or the flow rate at the second pressurized gas source adaptor is restored, switching the switching device to the first mixing mode. In this case, it can be determined according to whether the gas pressure at the second pressurized gas source adaptor is restored to determine whether to switch the switching device to the first mixing mode.

In addition, in the gas supply control method in another aspect of the present disclosure, the step of determining, according to the detected working state and a gas source test ventilation result, whether the gas pressure or a flow rate at the second pressurized gas source adaptor is restored specifically comprises: when the ventilator is in a standby state, determining whether the gas pressure or the flow rate at the second pressurized gas source adaptor satisfies a standby ventilation test; if yes, determining that the gas pressure or the flow rate at the second pressurized gas source adaptor is restored; when the ventilator is in the working state, performing a first ventilation test on the second pressurized gas source adaptor; if the first ventilation test is not passed, performing a second ventilation test on the second pressurized gas source adaptor; if the second ventilation test is not passed, determining that the gas pressure or the flow rate at the second pressurized gas source adaptor is not restored; and if the second ventilation test is passed, determining that the gas pressure or the flow rate at the second pressurized gas source adaptor is restored. In this case, it can be determined more effectively and accurately whether the gas pressure at the second pressurized gas source adaptor is restored.

In addition, in the gas supply control method in another aspect of the present disclosure, the standby ventilation test, the first ventilation test, and the second ventilation test are ventilation tests performed on the second pressurized gas source adaptor to determine whether the gas pressure or the flow rate at the second pressurized gas source adaptor and the time satisfy requirements. In this case, the gas pressure at the second pressurized gas source adaptor and the time can be used to implement a ventilation test at the second pressurized gas source adaptor.

In addition, in the gas supply control method in another aspect of the present disclosure, pressure and time requirements of the first ventilation test are lower than pressure and time requirements of the second ventilation test; or the flow rate requirement of the first ventilation test is higher than the flow rate requirement of the second ventilation test, and the time requirement of the first ventilation test is lower than the flow rate and time requirements of the second ventilation test. In this case, successful switching to the second mixing mode can be ensured.

According to the present disclosure, in this way, the ventilator and the gas supply control method of a ventilator can be independent of a central gas supply system, perform switching according to a gas supply source, and can provide a mixed gas with a desired oxygen concentration in time.

MAJOR REFERENCE NUMERALS

Figure 1:
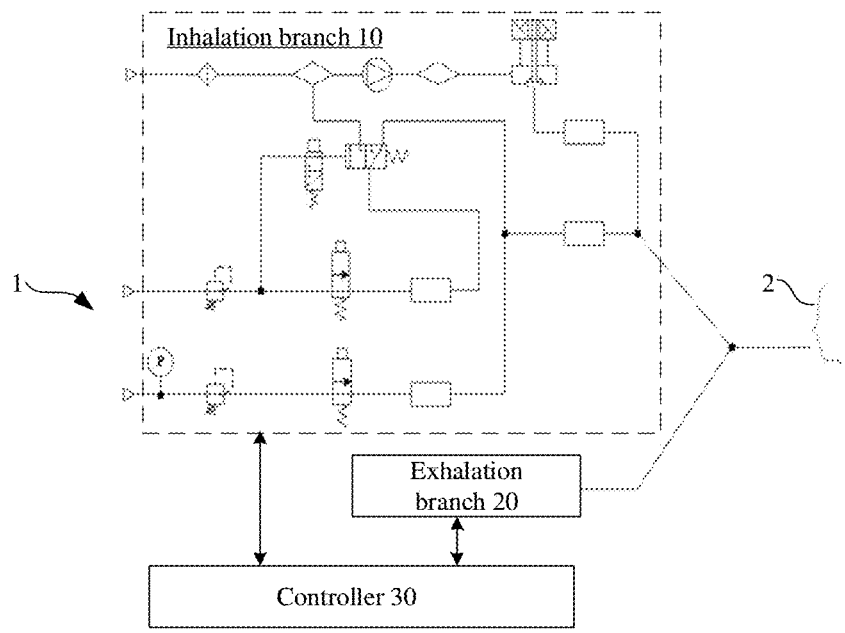
FIG. 1 is a system block diagram of a ventilator in an example 1 of the present disclosure.

1. ventilator, 2. patient, 10. inhalation branch, 20. exhalation branch, 20. controller, 11. first gas path, 12. second gas path, 13. third gas path, 14. switching device, 15. first inhalation branch, 16. second inhalation branch, and 17. drive gas path.

DETAILED DESCRIPTION OF EMBODIMENTS

The preferred implementations of the present disclosure are described below in detail with reference to the accompanying drawings. In the following description, the same components are provided with the same reference numerals. Repeated description is omitted. In addition, the accompanying drawings are schematic figures. The proportions among the sizes of the components, the shapes of the components, and the like may be different from those in reality.

FIG. 1 is a system block diagram of a ventilator 1 in an example 1 of the present disclosure. As shown in FIG. 1, in this implementation, the ventilator 1 may comprise an inhalation branch 10 and an exhalation branch 20. In the ventilator 1, the inhalation branch 10 may be configured to manage the inhalation of a patient 2 and can provide the patient 2 with a mixed gas with a desired oxygen concentration. The exhalation branch 20 may be configured to manage the exhalation of the patient 2 and can receive a gas exhaled by the patient 2.

In addition, the exhalation branch 20 may further comprise a controller 30. The controller 30 may control the action of the inhalation branch 10 and the exhalation branch 20 by using feedbacks from the inhalation branch 10 and the exhalation branch 20, to assist the patient 2 to complete inhalation or exhalation.

In this implementation, in the inhalation branch 10, a side near the patient 2 is defined as a "downstream side" or a "downstream end", and a side far away from the patient 2 is defined as an "upstream side" or an "upstream end". As described below, various types of supply gases (for example, high-pressure oxygen, high-pressure air or ambient air) are described on an upstream side of the inhalation branch 10. The supply gas is mixed to be supplied to the patient 2 on the downstream side along the inhalation branch 10.

Figure 2:
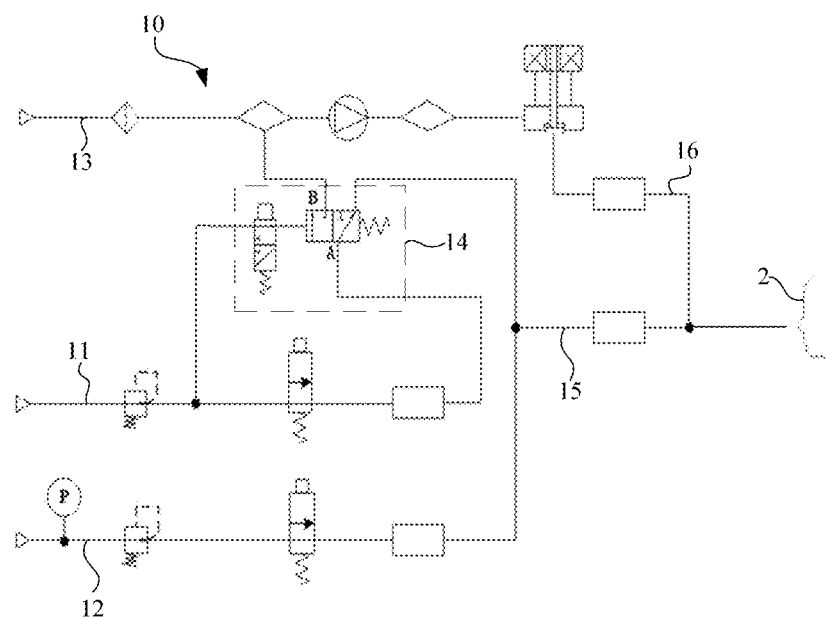
FIG. 2 is a schematic diagram of an inhalation branch in one embodiment of the present disclosure.
Figure 3:
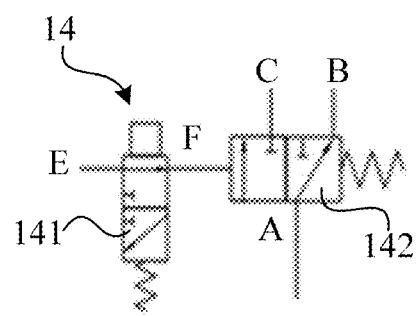
FIG. 3 is a schematic diagram of a switching device in one embodiment of the present disclosure.

FIG. 2 is a schematic diagram of the inhalation branch 10 in one embodiment of the present disclosure. FIG. 3 is a schematic diagram of a switching device 14 in one embodiment of the present disclosure.

In this implementation, as shown in FIG. 2, the inhalation branch 10 may comprise a first gas path 11, a second gas path 12, a third gas path 13, and a switching device 14. In the inhalation branch 10, switching among and gas mixing in the first gas path 11, the second gas path 12, and the third gas path 13 may be implemented by using the switching device 14.

In this implementation, the inhalation branch 10 further comprises a first inhalation branch 15 and a second inhalation branch 16. The switching device 14 may be used to implement a first mixing mode M1 in which the first gas path 11 and the second gas path 12 are connected to the first inhalation branch 15 and a second mixing mode M2 in which the first gas path 11 and the third gas path 13 are connected to the second inhalation branch 16 (described below).

Figure 4:
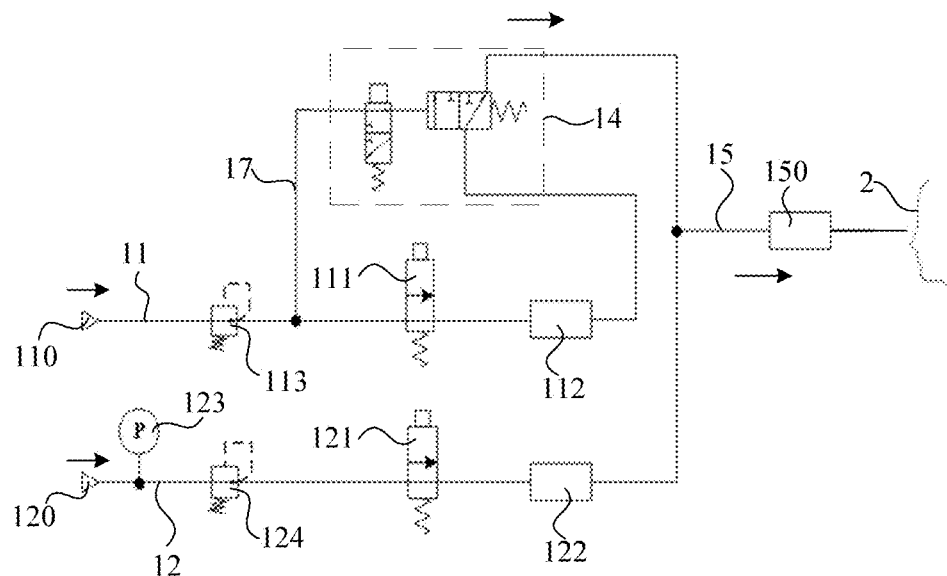
FIG. 4 is a schematic diagram of the inhalation branch in a first mixing mode in one embodiment of the present disclosure.

In this implementation, as shown in FIG. 2 and FIG. 4 that are described below, the first gas path 11 may comprise a first pressurized gas source adaptor 110 and a first flow adjustment device 111 connected in sequence. The first pressurized gas source adaptor 110 may receive a first pressure gas source. That is, the first pressurized gas source adaptor 110 may be connected to the first pressure gas source. In this way, the first pressure gas source can supply gas to the first gas path 11 via the first pressurized gas source adaptor 110. In some examples, the first pressure gas source may be high-pressure oxygen. In addition, in some examples, the first pressure gas source received by the first pressurized gas source adaptor 110 may be a bottled compressed gas.

In addition, in the first gas path 11, for example, a gas such as high-pressure oxygen may be delivered to the first flow adjustment device 111 through the first pressurized gas source adaptor 110. The first flow adjustment device 111 may adjust the flow of a second pressurized gas source received by the first pressurized gas source adaptor 110. In some examples, the first flow adjustment device 111 may be a solenoid proportional valve. However, this implementation is not limited thereto. For example, the first flow adjustment device 111 may be a valve group or a valve island switch formed by valves with different via diameters, a flow control valve formed by motors or the like.

In addition, the first gas path 11 may further comprise a first flow sensor 112. The first flow sensor 112 may measure the flow of a gas passing through the first flow adjustment device 111. In some examples, the controller 30 may further control the first flow adjustment device 111 according to a received flow value detected by the first flow sensor 112, to implement precise control of the flow. In some examples, the first flow sensor 112 may be an oxygen flow sensor. However, this implementation is not limited thereto. The first flow sensor 112 may be a flow sensor that can implement the same function.

In addition, in this implementation, the first gas path 11 may further comprise a first pressure regulating device 113. The first pressure regulating device 113 may be disposed between the first pressurized gas source adaptor 110 and the first flow adjustment device 111. In the first gas path 11, the first pressure regulating device 113 may regulate the pressure of the first pressure gas source, so that a gas with a desired pressure can be provided. In some examples, the first pressure regulating device 113 may be a pressure regulating valve. However, this implementation is not limited thereto. The first pressure regulating device 113 may be a pressure regulating device that can implement the same function.

In this implementation, as shown in FIG. 2 and FIG. 4, the second gas path 12 may comprise a second pressurized gas source adaptor 120 and a second flow adjustment device 121 connected in sequence. The second pressurized gas source adaptor 120 may receive the second pressurized gas source. That is, the second pressurized gas source adaptor 120 may be connected to the second pressurized gas source. In this way, the second pressurized gas source can supply gas to the second gas path 12 via the second pressurized gas source adaptor 120. In some examples, the second pressurized gas source may be high-pressure air or a high-pressure mixed gas of helium and oxygen. In some examples, the second pressurized gas source received by the second pressurized gas source adaptor 120 may be compressed air from a central gas supply system, for example, a central gas supply system of a hospital.

In the second gas path 12, a gas such as high-pressure air may be delivered to the second flow adjustment device 121 through the second pressurized gas source adaptor 120. The second flow adjustment device 121 may adjust the flow of the second pressurized gas source received by the second pressurized gas source adaptor 120. In some examples, the second flow adjustment device 121 may be a solenoid proportional valve. However, this implementation is not limited thereto. For example, the second flow adjustment device 121 may be a valve group or a valve island switch formed by valves with different via diameters, a flow control valve formed by motors or the like.

In addition, the second gas path 12 may further comprise a second flow sensor 122. The second flow sensor 122 may measure the flow of a gas passing through the second flow adjustment device 121. In some examples, the controller 30 may further control the second flow adjustment device 121 according to a received flow value detected by the second flow sensor 122, to implement precise control of the flow. In some examples, the second flow sensor 122 may be an air flow sensor. However, this implementation is not limited thereto. The second flow sensor 122 may be a flow sensor that can implement the same function.

In addition, in some examples, from the perspective of ensuring an oxygen concentration of a gas delivered to the patient 2, in the first mixing mode M1, a difference between a volume of a path from the first flow sensor 112 to a gas mixing device 150 (which is described below) and a volume of a path from the second flow sensor 122 to the gas mixing device 150 does not exceed, for example, 40 mL, and an internal accommodating cavity when the switching device 14 is switched to the first mixing mode M1 does not exceed, for example, 30 mL.

As shown in FIG. 4, the second gas path 12 further comprises a pressure sensor 123 detecting gas pressure at the second pressurized gas source adaptor 120. That is, in the second gas path 12, the pressure sensor 123 may measure the pressure of the second pressurized gas source received by the second pressurized gas source adaptor 120. In addition, pressure information (a measured value) obtained by the pressure sensor 123 can be delivered to the controller 30. In this way, the controller 30 can control the switching device 14 based on the measured value of the pressure sensor 123, to enable the switching device 14 to switch between the first mixing mode M1 and the second mixing mode M2. In addition, the pressure sensor 123 may be a pressure switch.

In addition, in this implementation, the second gas path 12 may further comprise a second pressure regulating device 124. In addition, the second pressure regulating device 124 may be disposed between the pressure sensor 123 and the second flow adjustment device 121. The second pressure regulating device 124 may regulate the pressure of the second pressurized gas source received by the second pressurized gas source adaptor 120. In some examples, the second pressure regulating device 124 may be a pressure regulating valve. However, this implementation is not limited thereto. The second pressure regulating device 124 may be a pressure regulating device that implements the same function.

In this implementation, the third gas path 13 may comprise a third pressurized gas source adaptor 130. The third pressurized gas source adaptor 130 may receive a third pressure gas source. That is, the third pressurized gas source adaptor 130 may be connected to the third pressure gas source. In this way, the third pressure gas source can supply gas to the third gas path 13 via the third pressurized gas source adaptor 130. In some examples, the third pressure gas source may be ambient air. For example, the ambient air may be ambient air in a hospital.

Figure 6:
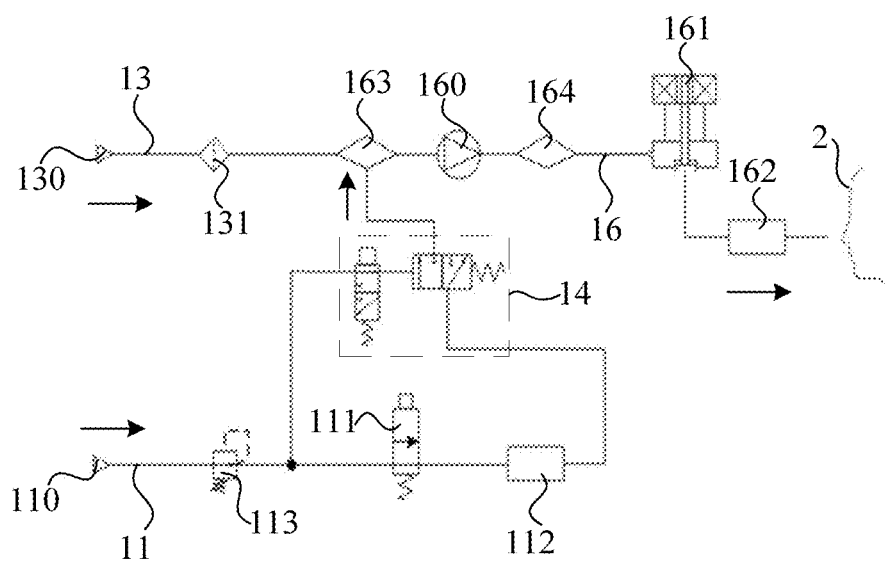
FIG. 6 is a schematic diagram of the inhalation branch in a second mixing mode in one embodiment of the present disclosure.

In addition, as shown in FIG. 6 that is described below, the third gas path 13 may further be provided with a filtering device 131. The filtering device 131 may filter the third pressure gas source, for example, ambient air, received by the third pressurized gas source adaptor 130. The filtering device 131 can be used to generate air that conforms to specified standards, for example, air that conforms to medical hygiene standards. In some examples, the filtering device 131 may be a high efficiency particulate air (HEPA) filter.

In this implementation, the air pressure of the first pressure gas source supplied to the first pressurized gas source adaptor 110 is set to P1 (a first pressure), the air pressure of the second pressurized gas source supplied to the second pressurized gas source adaptor 120 is set to P2 (a second pressure), and the air pressure of the third pressure gas source supplied to the third pressurized gas source adaptor 130 is set to P3 (the second pressure). The air pressure P1 may be greater than the air pressure P3, and the air pressure P2 may be greater than the air pressure P3.

In addition, in this implementation, the gas having the air pressure P1 or the air pressure P2 is considered as a high-pressure gas. In one embodiment, the air pressure P1 or the air pressure P2 is in a range of 280 kPa to 650 kPa. In addition, a gas having the air pressure P3 is considered as a non-high-pressure gas.

In addition, if the second pressurized gas source adaptor 120 is introduced into the central gas supply system, the second pressure (the air pressure P2) may change as the pressure of the central gas supply system changes. In the ventilator 1 in this implementation, when the switching device 14 is in the first mixing mode M1 and the air pressure P2 is lower than a specified value, the controller 30 can control the switching device 14, so as to switch from the first mixing mode M1 to the second mixing mode M2 (which is described below).

In this implementation, the first inhalation branch 15 may deliver inhalation gas (for example, an oxygen-containing mixed gas) to a patient. When the switching device 14 is in the first mixing mode M1 (which is described below), the first gas path 11 and the second gas path 12 are connected to (in communication with) the first inhalation branch 15. In this case, a gas from the first gas path 11 and a gas from the second gas path 12 enter the first inhalation branch 15 to be mixed and supplied to the patient 2.

In addition, the first inhalation branch 15 may comprise a gas mixing device 150. In this case, the gas (the first pressure gas source) from the first gas path 11 and from the gas (the second pressurized gas source) from the second gas path 12 can further be mixed to obtain a mixed gas with an improved mixing effect.

In this implementation, the second inhalation branch 16 may deliver inhalation gas (for example, an oxygen-containing mixed gas) to a patient. When the switching device 14 is in the second mixing mode M2 (which is described below), the first gas path 11 and the third gas path 13 are connected to (in communication with) the second inhalation branch 16. In this case, the gas from the first gas path 11 and the gas from the third gas path 12 enter the second inhalation branch 16 to be mixed and supplied to the patient 2.

In this implementation, the second inhalation branch 16 may further comprise a gas compression device 160 (referring to FIG. 6). The gas compression device 160 can compress and pressurize a gas flowing through the second inhalation branch 16. A maximum static output pressure of the gas compression device 160 is less than 210 cm H20(1 cm H20=0.098 kPa); and in one embodiment, the maximum static output pressure of the gas compression device 160 is less than 140 cm H20. In this way, the ventilator can generate less noise and has lower power consumption, a smaller volume, and a lighter weight. In some examples, the gas compression device 160 may be a gas compression device, for example, a turbine, that has a relatively low maximum static output pressure. However, this implementation is not limited thereto. The gas compression device 160 may be another device, for example, a light duty compressor, that completes the same function.

In this implementation, the second inhalation branch 16 may further comprise a third flow adjustment device 161. The third flow adjustment device 161 may control the flow of the gas flowing through the second inhalation branch 16. In some examples, the third flow adjustment device 161 may be a flow control valve formed by motors. However, this implementation is not limited thereto. For example, the third flow adjustment device 161 may be a valve group or a valve island switch formed by valves with different via diameters, a solenoid proportional valve or the like.

In addition, the second inhalation branch 16 may further comprise a third flow sensor 162. The third flow sensor 162 may measure the flow of a gas passing through the third flow adjustment device 161. In addition, in some examples, the third flow sensor 162 may be an air flow sensor. However, this implementation is not limited thereto, and may be another flow sensor that completes the same function.

In addition, the second inhalation branch 16 may further comprise a first mixing cavity 163. In the second mixing mode M2, the switching device 14 enables the first gas path 11 and the third gas path 13 to be connected to (in communication with) the second inhalation branch 16 by the first mixing cavity 163. That is, the gas supplied by the first gas path 11 and the gas supplied by the third gas path 13 are mixed in the first mixing cavity 163. In this way, a mixed gas with an improved mixing effect can be obtained, so that the mixed gas with a desired oxygen concentration is provided to the patient 2. In some examples, when the gas supplied to the first gas path 11 is oxygen, the first mixing cavity 163 may be an oxygen-mixing cavity.

In addition, the second inhalation branch 16 may further comprise a second mixing cavity 164. The second mixing cavity 164 is configured to mix the mixed gas that is in the second mixing mode M2 and is pressurized by the gas compression device 160 during inhalation. In this way, the mixing effect of the mixed gas can further be improved. In some examples, when the gas supplied to the first gas path 11 is oxygen, the second mixing cavity 164 may be an oxygen-mixing cavity.

Figure 5:
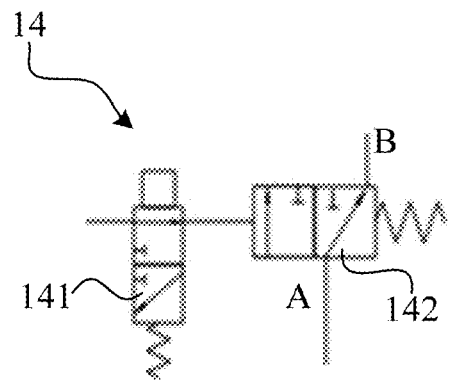
FIG. 5 is a schematic state diagram of the switching device shown in FIG. 4.
Figure 7:
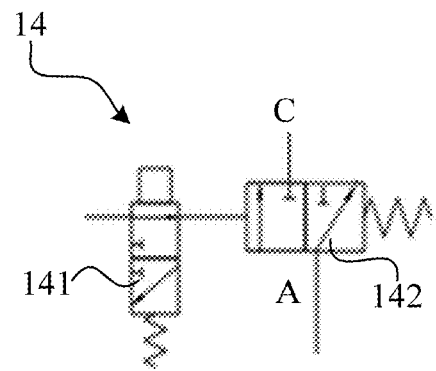
FIG. 7 is a schematic state diagram of a switching device shown in FIG. 6.

The switching device 14 and a switching mode thereof are described below in detail with reference to FIG. 4 to FIG. 7. FIG. 4 is a schematic diagram of the inhalation branch in a first mixing mode in one embodiment of the present disclosure. FIG. 5 is a schematic state diagram of the switching device shown in FIG. 4. FIG. 6 is a schematic diagram of the inhalation branch in a second mixing mode in one embodiment of the present disclosure. FIG. 7 is a schematic state diagram of a switching device shown in FIG. 6.

As shown in FIG. 4 and FIG. 6, the switching device 14 has the first mixing mode M1 in which the first gas path 11 and the second gas path 12 are connected to the first inhalation branch 15 (referring to FIG. 4) and the second mixing mode M2 in which the first gas path 11 and the third gas path 13 are connected to the second inhalation branch 16 (referring to FIG. 6). In some examples, the controller 30 may control the switching device 14 based on the measured value of the pressure sensor 123 disposed on the second gas path 12, to enable the switching device 14 to switch between the first mixing mode M1 and the second mixing mode M2.

Specifically, the controller 30 may control the switching device 14 based on the measured value of the pressure sensor 123 in some cases (for example, a case in which the measured value of the pressure sensor 123 is in a normal range), to enable the switching device 14 to be in the first mixing mode M1 (referring to FIG. 4). In this case, the first gas path 11 and the second gas path 12 are in communication with the first inhalation branch 15, and a supply gas is delivered to the first inhalation branch 15 along the first gas path 11 and the second gas path 12 (the direction of the linear arrow shown in FIG. 4) and is provided to the patient 2, so that the patient 2 can obtain, for example, the mixed gas with a desired oxygen concentration.

In addition, the controller 30 may control the switching device 14 based on the measured value of the pressure sensor 123 in some other cases (for example, the case in which the measured value of the pressure sensor 123 is in a normal range), to enable the switching device 14 to be in the second mixing mode M2 (referring to FIG. 6). In this case, the first gas path 11 and the third gas path 13 are in communication with the second inhalation branch 16, and a supply gas is delivered to the second inhalation branch 16 along the first gas path 11 and the third gas path 13 (the direction of the linear arrow shown in FIG. 6) and is provided to the patient 2, so that the patient 2 can obtain, for example, the mixed gas with a desired oxygen concentration.

Referring to FIG. 3 again, in this implementation, the switching device 14 may comprise a pilot valve 141 and a pneumatic three-way valve 142. In addition, the pilot valve 141 may be controlled by the controller 30. The pilot valve 141 is connected to the pneumatic three-way valve 142. The pilot valve 141 can be controlled to pneumatically implement different connection paths of the pneumatic three-way valve 142.

Specifically, the pilot valve 141 has connecting ends E and F. The connecting end E may be in communication with the first gas path 11 via a drive gas path 17; and the connecting end F is connected to the pneumatic three-way valve 142 and is configured to drive the pneumatic three-way valve 142. In addition, the pneumatic three-way valve 142 comprises a gas inlet end A and two gas outlet ends B and C. The gas inlet end A of the pneumatic three-way valve 142 may be connected to the first gas path 11, the gas outlet end B may be connected to the second gas path 12, and the gas outlet end C may be connected to the third gas path 13. In addition, this implementation is not limited thereto. For example, the gas inlet end A of the pneumatic three-way valve 142 may be connected to the first gas path 11, the gas outlet end C may be connected to the second gas path 12, and the gas outlet end B may be connected to the third gas path 13. In this case, the switching device 14 can also implement switching between the first mixing mode M1 and the second mixing mode M2.

As shown in FIG. 4, the drive gas path 17 may be a manifold of the first gas path 11, and the first gas path 11 supplies gas to the drive gas path. In addition, this implementation is not limited to that the first gas path 11 supplies a gas to the drive gas path 17, the second gas path 12 may supply gas to the drive gas path, or a separate gas path may supply gas to the drive gas path.

In addition, in some examples, for example, the pilot valve 141 is a solenoid valve. The solenoid valve may be turned on or turn off under the effect of the controller 30. After the pilot valve 141 is turned on, the pressure-regulated first pressure gas source from the first gas path 11 drives the pneumatic three-way valve 142 via the drive gas path 17, to enable the first gas path 11 and the second gas path 12 to be connected to (in communication with) the first inhalation branch 15. That is, the gas from the first gas path 11 and the gas from the second gas path 12 converge to enter the first inhalation branch 15. In this case, the switching device 14 is in the first mixing mode M1 (referring to FIG. 4). In addition, after the pilot valve 141 is turned off, the drive gas path 17 is disconnected from the pneumatic three-way valve 142. Under the effect of an elastic force, the pneumatic three-way valve 142 enables the first gas path 11 and the third gas path 13 to be connected to (in communication with) the second inhalation branch 16. That is, the gas from the first gas path 11 and the gas from the third gas path 13 converge to enter the second inhalation branch 16. In this case, the switching device 14 is in the second mixing mode M2 (referring to FIG. 6).

As discussed above, in this implementation, the controller 30 can control the switching device 14 based on the measured value of the pressure sensor 123, to enable the switching device 14 to switch between the first mixing mode M1 in which the first gas path 11 and the second gas path 12 are connected to the first inhalation branch 15 and the second mixing mode M2 in which the first gas path 11 and the third gas path 13 are connected to the second inhalation branch 16. In this way, switching can be performed according to a gas supply source and for example, the mixed gas with a desired oxygen concentration can be provided in time.

In some examples, when the controller 30 detects that the value measured by the pressure sensor 123 satisfies the specified value (for example, the pressure value is greater than 200 kPa), the controller 30 enables the pilot valve 141 to be turned on, the gas from the drive gas path 17 directly drives, for example, an internal spring of the pneumatic three-way valve 142, to enable the gas inlet end A of the pneumatic three-way valve 142 to be in communication with the gas outlet end B, so as to enable the switching device 14 to be in the first mixing mode M1 in which the first gas path 11 and the second gas path 12 are connected to (in communication with) the first inhalation branch 15. In some other examples, when the controller 30 detects that the value measured by the pressure sensor 123 does not satisfy the specified value (for example, the pressure value is less than or equal to 200 kPa), the controller 30 enables the pilot valve 141 to be turn off. In this case, the gas from the drive gas path 17 is disconnected from the pneumatic three-way valve 142, the internal spring of the pneumatic three-way valve 142 is restored, to enable the gas inlet end A of the pneumatic three-way valve 142 to be in communication with the gas outlet end C, so as to enable the switching device 14 to be in the second mixing mode M2 in which the first gas path 11 is connected to the third gas path 13 and the second inhalation branch 16. In this way, switching can be performed according to a gas supply source and a mixed gas with a desired oxygen concentration can be provided in time. In addition, independence of a central gas supply system can further be implemented.

In addition, the switching device 14 in this implementation is not limited to the example described above. A variant of the switching device 14 in this implementation is described below with reference to FIG. 8 and FIG. 9.

Figure 8:
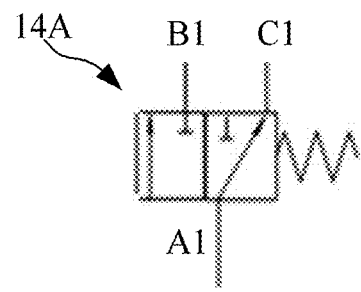
FIG. 8 is a schematic diagram of a variant 1 of a switching device in one embodiment of the present disclosure.

FIG. 8 is a schematic diagram of a variant 1 of a switching device in one embodiment of the present disclosure. As shown in FIG. 8, the switching device 14 may be a solenoid three-way valve 14A used in place of the pilot valve 141 and the pneumatic three-way valve 142. In this case, the controller 30 directly controls the solenoid three-way valve 14A, and communication between a gas inlet end A1 and a gas outlet end B1 or a gas outlet end C1 of the solenoid three-way valve 14A can also be implemented. In this way, the switching device 14 implements switching between the first mixing mode M1 and the second mixing mode M2. In addition, when the solenoid three-way valve 14A is used, the drive gas path 17 in this implementation is further omitted.

Figure 9:
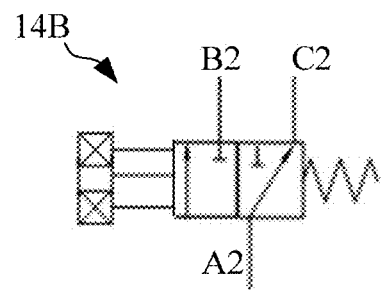
FIG. 9 is a schematic diagram of a variant 2 of a switching device in one embodiment of the present disclosure.

FIG. 9 is a schematic diagram of a variant 2 of a switching device in one embodiment of the present disclosure. As shown in FIG. 9, the switching device 14 may be a motor-driven three-way valve 14B used in place of the pilot valve 141 and the pneumatic three-way valve 142. That is, the switching device 14 may be a motor-controlled three-way valve. In this case, the controller 30 directly controls the motor-driven three-way valve 14B, and communication between a gas inlet end A2 and a gas outlet end B2 or a gas outlet end C2 of the motor-driven three-way valve 14B can also be implemented. In this way, the switching device 14 implements switching between the first mixing mode M1 and the second mixing mode M2. In addition, when the motor-driven three-way valve 14B is used, the drive gas path 17 in this implementation is further omitted.

Figure 10:
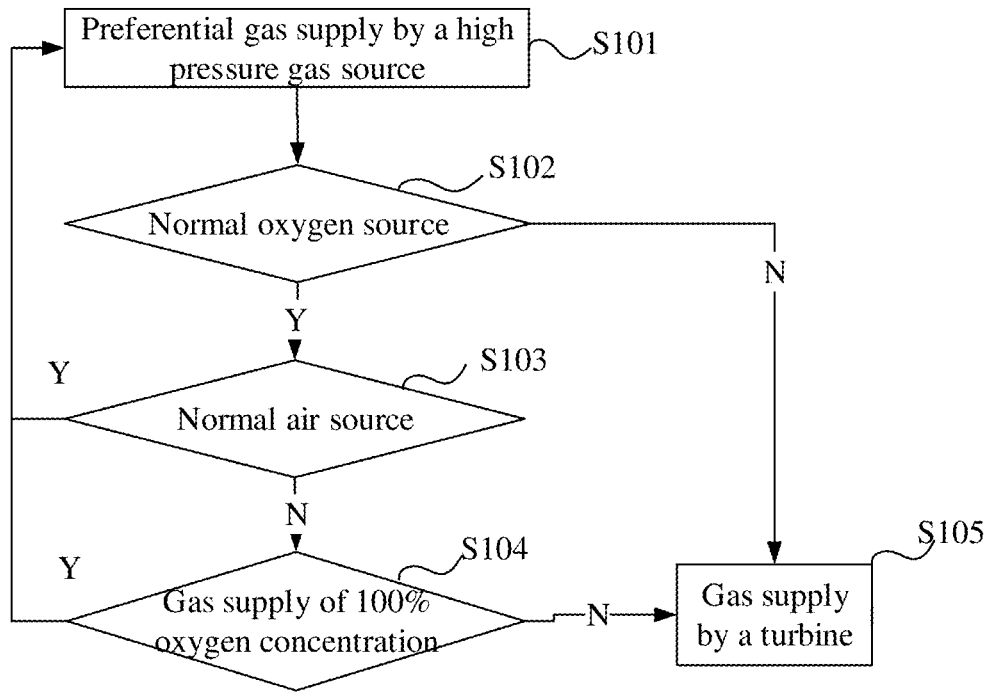
FIG. 10 is a flowchart of preferential gas supply by a high-pressure gas source in a gas supply control method of a ventilator in one embodiment of the present disclosure.
Figure 11:
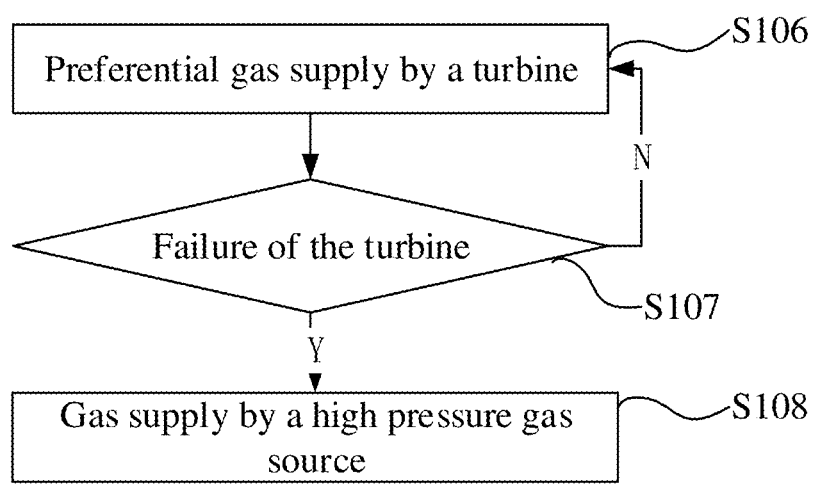
FIG. 11 is a flowchart of preferential gas supply by a turbine in a gas supply control method of a ventilator in one embodiment of the present disclosure.

FIG. 10 is a flowchart of preferential gas supply by a high-pressure gas source in a gas supply control method of a ventilator in one embodiment of the present disclosure. FIG. 11 is a flowchart of preferential gas supply by a turbine in a gas supply control method of a ventilator in one embodiment of the present disclosure.

As discussed above, a gas supply source of the ventilator 1 in this implementation comprises a first pressure gas source supplying a gas to the first gas path 11, a second pressurized gas source supplying a gas to the second gas path 12, and a third pressure gas source supplying a gas to the third gas path 13. In this implementation, the first pressure gas source may be a high-pressure oxygen source, the second pressurized gas source may be a high-pressure air source, and the third pressure gas source may be an ambient air source. In the gas supply control method of the ventilator 1 in this implementation, switching may be performed among high-pressure oxygen, high-pressure air, and ambient air (a turbine gas source).

In the ventilator, the controller 30 may perform the following steps: when the switching device 14 is in the first mixing mode M1, detecting a working state of the ventilator 1 and gas pressure at the second pressurized gas source adaptor 120; determining, according to the detected working state of the ventilator 1 and the detected gas pressure at the second pressurized gas source adaptor 120, whether the gas pressure at the second pressurized gas source adaptor 120 is adequate; and when the gas pressure at the second pressurized gas source adaptor 120 is inadequate, switching the switching device 14 to the second mixing mode M2. Herein, the working state of the ventilator 1 may be detected regularly. However, this implementation is not limited thereto. The working state of the ventilator 1 may be detected irregularly.

The step of determining, according to the detected working state of the ventilator and the detected gas pressure at the second pressurized gas source adaptor 120, whether the gas pressure at the second pressurized gas source adaptor 120 is adequate specifically comprises: when the ventilator 1 is in a standby state, determining whether the gas pressure at the second pressurized gas source adaptor 120 satisfies a standby pressure threshold and a standby time threshold; if yes, determining that the gas pressure at the second pressurized gas source adaptor 120 is adequate; if not, determining that the gas pressure at the second pressurized gas source adaptor 120 is inadequate; when the ventilator 1 is in the working state, determining whether the gas pressure at the second pressurized gas source adaptor 120 satisfies a first working pressure threshold and a first working time threshold; if not, determining whether the gas pressure at the second pressurized gas source adaptor 120 satisfies a second working pressure threshold and a second working time threshold; if not, determining that the gas pressure at the second pressurized gas source adaptor is inadequate; and if yes, determining that the gas pressure at the second pressurized gas source adaptor 120 is adequate. In addition, in this implementation, the first working pressure threshold may be less than the second working pressure threshold, and the first working time threshold may be less than the second working time threshold.

Specifically, in this implementation, the switching device 14 provides the first mixing mode M1 (referred to as "preferential gas supply by a high-pressure gas source" or "gas supply by a high-pressure gas source" hereinafter) and the second mixing mode M2 (referred to as "preferential gas supply by a turbine gas source" or "gas supply by a turbine" hereinafter). In the case of the preferential gas supply by a high-pressure gas source, as shown in FIG. 10 and FIG. 11, the switching device first determines whether the first pressure gas source (for example, an oxygen source) is normal (block S102), if not, switches to the gas supply by a turbine (block S105), if the oxygen source is normal, determines whether the second pressurized gas source (for example, an air source) is normal (block S103), if the air source is normal or 100% oxygen concentration gas supply is set (block S104), keeps ventilation with the high-pressure gas source, and if the air source is not normal, switches to the gas supply by a turbine (block S105). In the case of the preferential gas supply by a turbine, as shown in FIG. 11, the switching device determines whether the turbine works normally (block S107), if yes, keeps the gas supply by a turbine, and if not, switches to the gas supply by the high-pressure gas source (block S108). In addition, in some examples, in the case of the gas supply by a turbine, gas supply by the first pressure gas source (for example, an oxygen source) may be not required, but instead, the turbine separately supplies a gas.

In addition, the step of determining, according to the detected working state and a gas source test ventilation result, whether the gas pressure at the second pressurized gas source adaptor is restored specifically comprises: when the ventilator 1 is in a standby state, determining whether the gas pressure at the second pressurized gas source adaptor 120 satisfies a standby ventilation test; if yes, determining that the gas pressure at the second pressurized gas source adaptor 120 is restored; when the ventilator 1 is in the working state, performing a first ventilation test on the second pressurized gas source adaptor 120; if the first ventilation test is not passed, performing a second ventilation test on the second pressurized gas source adaptor; if the second ventilation test is not passed, determining that the gas pressure at the second pressurized gas source adaptor 120 is not restored; and if the second ventilation test is passed, determining that the gas pressure at the second pressurized gas source adaptor 120 is restored.

In addition, the standby ventilation test, the first ventilation test, and the second ventilation test are ventilation tests performed on the second pressurized gas source adaptor to determine whether the gas pressure at the second pressurized gas source adaptor and the time satisfy requirements. In addition, pressure and time requirements of the first ventilation test may be lower than pressure and time requirements of the second ventilation test.

In some examples, in a ventilation test, another constant flow rate, for example, 10 liters per minute or 100 liters per minute, may be used to test the value of flow rate ventilation. In addition, in the ventilation test, a variable flow rate may be used for the value of the flow rate ventilation, and comprises, for example, a linearly variable flow rate, and a sinusoidally variable flow rate. For example, the flow rate is increased from 10 liters per minute to 100 liters per minute.

In addition, in the ventilation test, if a flow rate form is variable, and a sinusoidal change is similar to a flow rate form of the ventilation of the ventilator. In this case, it is detected whether a gas source pressure satisfies a pressure threshold at this flow rate. In addition, in some examples, in a ventilation test, another time length for determining the flow rate ventilation is, for example, 10 seconds, 30 seconds or the like.

Figure 12:
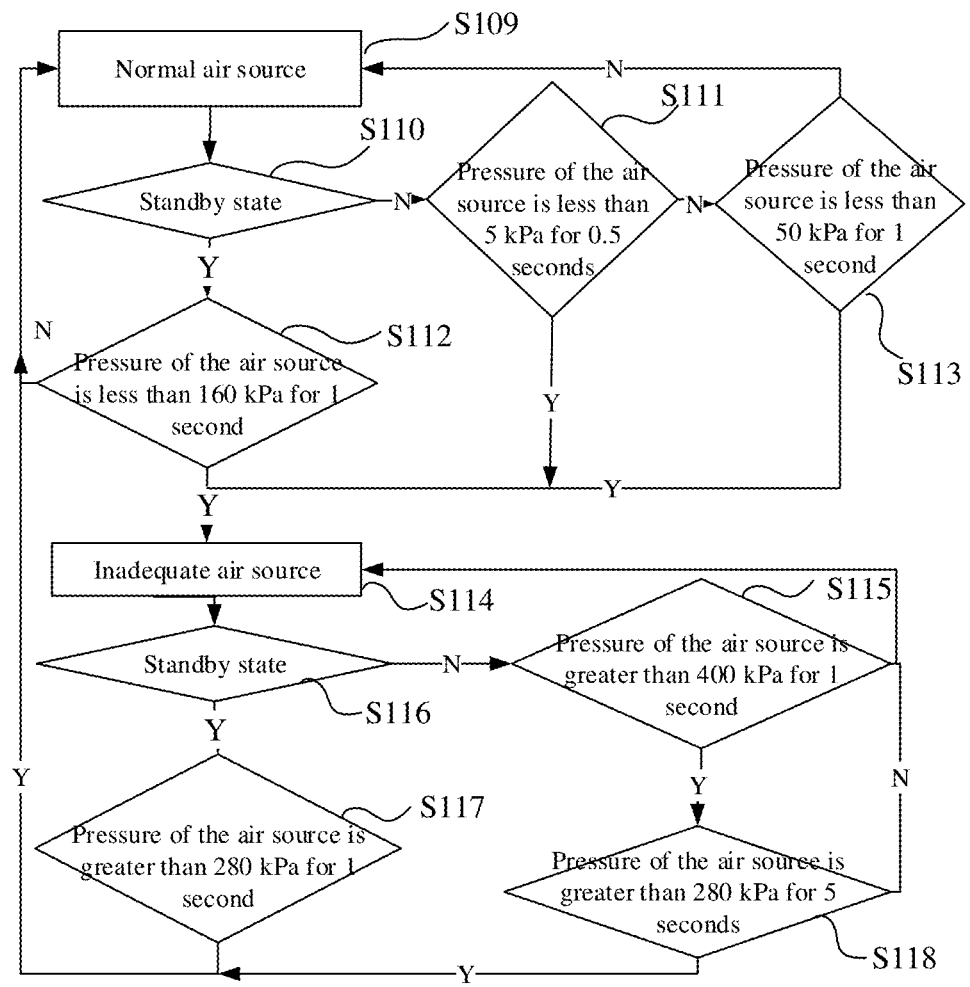
FIG. 12 is a flowchart of determination of an inadequate air source and a restoration strategy in a gas supply control method of a ventilator in one embodiment of the present disclosure.
Figure 13:
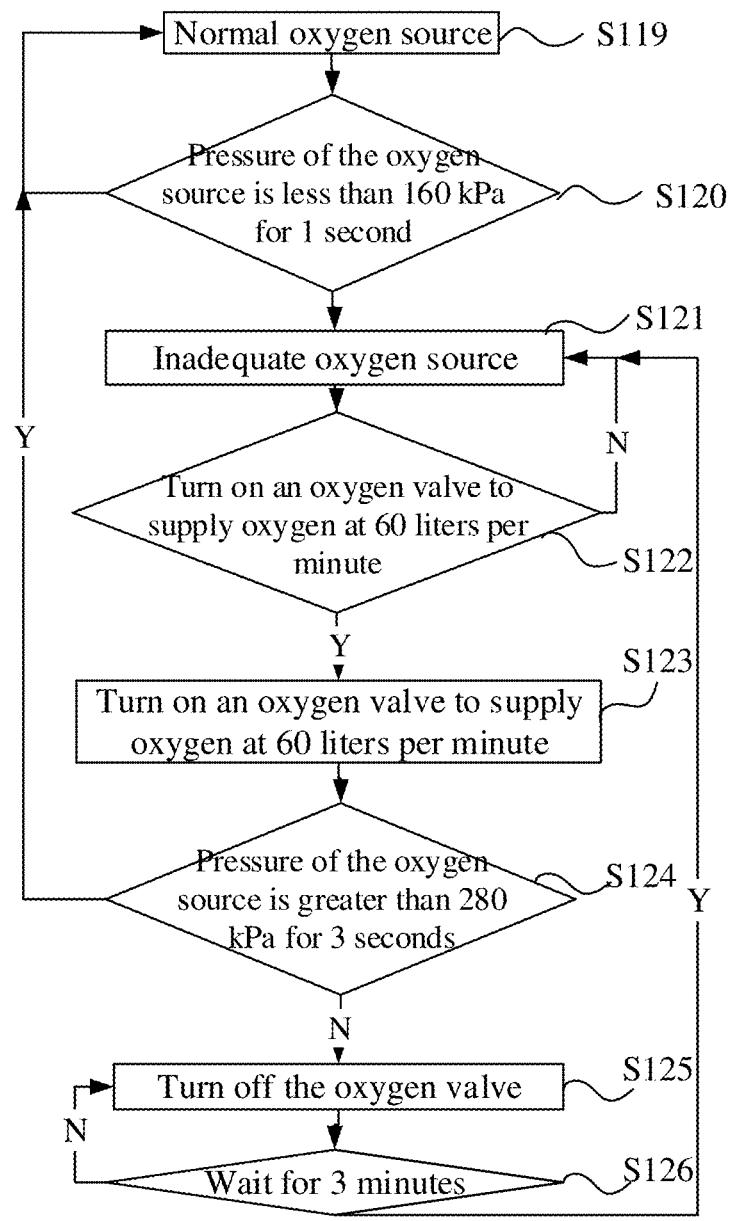
FIG. 13 is a flowchart of determination of an inadequate oxygen source and a restoration strategy in a gas supply control method of a ventilator in one embodiment of the present disclosure.

FIG. 12 is a flowchart of determination of an inadequate air source and a restoration strategy in a gas supply control method of a ventilator in one embodiment of the present disclosure. FIG. 13 is a flowchart of determination of an inadequate oxygen source and a restoration strategy in a gas supply control method of a ventilator in one embodiment of the present disclosure.

In addition, as shown in FIG. 12 and FIG. 13, in an example of determining that the second pressurized gas source, for example, the air source, is inadequate, in a standby state (block S110), it is detected that the pressure of the air source, for example, lasts 1 second and is less than 160 kPa (block S112). Herein, the selection of a pressure value is related to accessories selected for a used gas source and gas path; and an empirical value is selected for the time, and the time may be in a value range of 0.1 seconds to 1 second. Certainly, if a response speed requirement is not very high, the value range of the time may be 1 second to 10 minutes, and in this case, it is determined that the air source is inadequate, or otherwise the air source is normal. In a non-standby state (the ventilation state) (block S110), when it is detected that the pressure of the air source, for example, lasts 0.5 seconds and is less than 5 kPa (block S111) (5 kPa is a pressure value when an air cylinder is empty), it is determined that the air source is inadequate, or otherwise, it is then determined whether the pressure of the air source lasts 1 second and is less than 50 kPa (the pressure value is a gas source pressure in a typical working state for maintaining an adult, and the value can be lower for a baby or child) (block S113). If yes, it is determined that the air source is inadequate, or otherwise, the air source is normal.

In addition, in an example of restoration when the second pressurized gas source, for example, the air source, is inadequate, in a standby state (block S116), when it is detected that the pressure of the air source, for example, lasts 1 s and is greater than 280 kPa (the pressure value is a minimum value for the second pressurized gas source to work) (block S117), gas supply of the air source is restored, or otherwise, the air source is kept inadequate. In a non-standby state (the ventilation state) (block S116), when it is detected that the pressure of the air source, for example, lasts 1 s and is greater than 400 kPa (block S115), the gas supply of the air source is restored, or otherwise, it is determined whether the detected pressure of the air source, for example, lasts 5 seconds and is greater than 280 kPa (block S118), if yes, the gas supply of the air source is restored, or otherwise, the air source is kept inadequate.

In addition, in an example of determining that the first pressure gas source, for example, the oxygen source is inadequate and a restoration strategy, as shown in FIG. 13, for determination of whether the oxygen source is inadequate, when it is detected that the pressure of the oxygen source, for example, lasts 1 second and is less than 160 kPa (block S120), it is determined that the oxygen source is inadequate, or otherwise, it is determined that the oxygen source is normal (block S119). In an example of determination to restore the oxygen source, it is first determined whether the detected pressure of the oxygen source is greater than 280 kPa (block S122), if not, the oxygen source is kept inadequate, and if yes, gas source test ventilation is further performed. That is, an oxygen valve is turned on to deliver a gas at 60 LPM for 3 seconds (block S123). It is detected whether the pressure of the oxygen source lasts 3 seconds and is greater than 280 kPa, if yes, it is determined that the oxygen source is normal. If not, the oxygen proportional valve is turned off (block S125), and the oxygen source is tested again after a wait of 3 minutes (block S121).

In addition, in some examples, the switching device 14 may use a motor-controlled pneumatic three-way valve or use a solenoid three-way valve. In this case, it can be determined, without performing gas source test ventilation, whether the oxygen source is restored.

In this implementation, a combined value of segmented pressure thresholds and a time delay may be used to determine that the gas source is inadequate. Generally, a pressure switch or a pressure sensor is used to directly determine the status of a gas source. If a threshold is excessively low, a determination speed tends to be slow. If a threshold is excessively high, a determination tends to be incorrect. When the combined value of segmented pressure thresholds and a time delay is used for determination, the determination efficiency can be improved, and when the gas source pressure is lower, the determination speed is faster.

In addition, the restoration of the gas source is determined through experimental ventilation and a pressure change of the gas source. Switching is performed only when it is determined that the gas source is stably restored, to prevent incorrect recognition of the restoration of the gas source, thereby preventing frequent switching between the first pressure gas source and the third pressure gas source and the impact of repeated switching on the ventilation effect of the device.

In addition, the determination of whether the gas source is restored is not limited to the foregoing method. A gas source pressure switch may be used in place of a gas source pressure sensor and used in combination with flow rate detection. For example, it may be detected whether a flow rate exceeds 60 LPM within a particular time. In addition, in this implementation, during the setting, when the flow rate is higher, required duration may be shorter. In addition, segmented detection may be used. When it is determined that the flow rate does not exceed 100 LPM within 200 ms, it is then detected whether the flow rate can exceed 80 LPM within 500 ms, and if not, it is then detected whether the flow of 60 PLM can be maintained within 1 s. If the flow rate can meet a requirement, it is determined that the gas source is restored without needing to continue with subsequent detection. In this implementation, the values are not limited thereto.

In addition, in this implementation, the first pressure gas source is used to drive the pneumatic three-way valve 142. Therefore, gas source test ventilation needs to be performed for the first pressure gas source, or otherwise does not need to be performed. If the second pressurized gas source is used to drive the pneumatic three-way valve, gas source test ventilation needs to be performed to detect whether the second pressurized gas source is restored. If the switching device 14 does not use the pilot valve 141, the gas source test ventilation may be not required.

In addition, in the gas supply control method in this implementation, in some examples, when any high-pressure gas source (the first pressure gas source or the second pressurized gas source) is not available, one remaining normal high-pressure gas source may be selected without turning on gas supply by a turbine.

Figure 14:
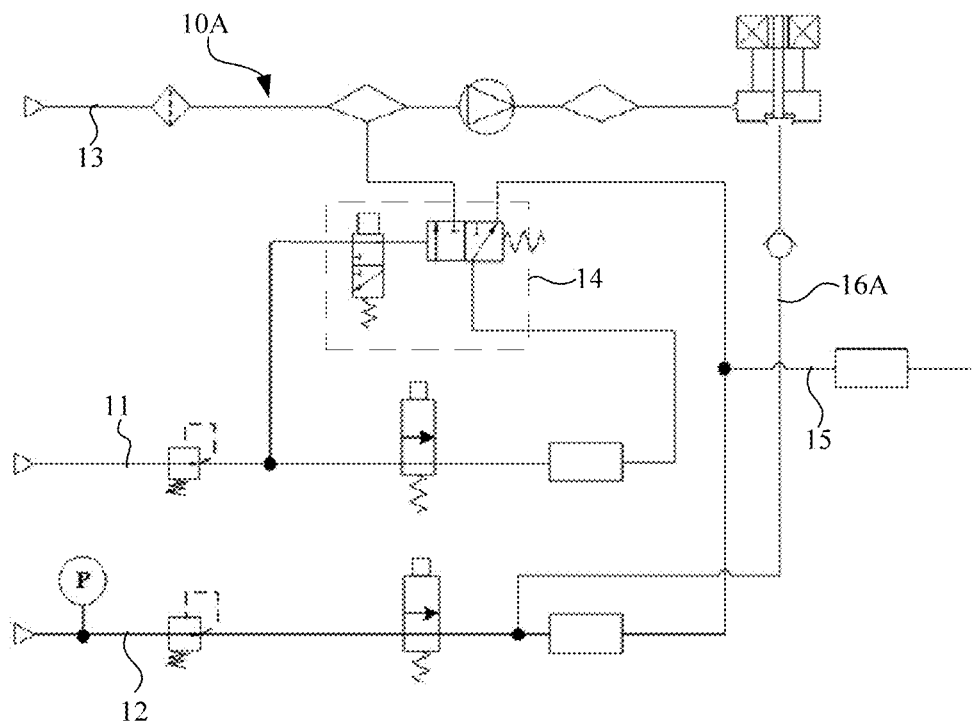
FIG. 14 is a schematic diagram of an inhalation branch in an example 2 of the present disclosure.
Figure 15:
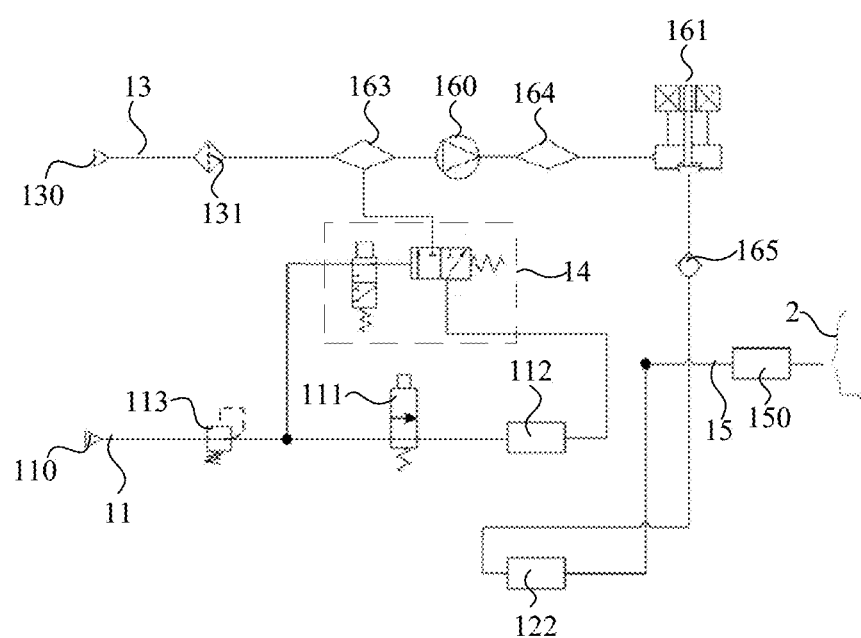
FIG. 15 is a schematic diagram of an inhalation branch in a second mixing mode in the example 2 of the present disclosure.

FIG. 14 is a schematic diagram of an inhalation branch in an example 2 of the present disclosure. FIG. 15 is a schematic diagram of an inhalation branch in a second mixing mode in the example 2 of the present disclosure.

A difference between an inhalation branch 10A in this implementation and the inhalation branch 10 in one embodiment is that a second inhalation branch 16A is different from the second inhalation branch 16 in one embodiment. That is, in the second inhalation branch 16A in this implementation, the third flow adjustment device 161 is connected to the second flow adjustment device 121, and the third flow adjustment device 161 is connected to the second flow sensor 122 (referring to FIG. 14). In addition, a one-way valve 165 may further be provided between the third flow adjustment device 161 and the second flow sensor 122. In addition, the third flow sensor 162 in one embodiment is further omitted in the second inhalation branch 16A. In this case, for the inhalation branch 10A in this implementation, switching can be performed according to a gas supply source and a mixed gas with a desired oxygen concentration can be provided in time.

In this implementation, the one-way valve 165 is turned on from an upstream side to a downstream side of the second inhalation branch 16A. In this way, a gas flowing from the upstream side to the downstream side of the second inhalation branch 16A can flow through the one-way valve 165. In addition, the one-way valve 165 is turned off from the downstream side to the upstream side of the second inhalation branch 16A. In this case, a gas on the downstream side cannot pass through the one-way valve 165 to flow into the second inhalation branch 16A.

In addition, particularly, in the case of the first mixing mode M1, the one-way valve 165 may effectively isolate the second gas path 12 from the second inhalation branch 16, to reduce the volume of an accommodating cavity of the second gas path 12, so as to enable the impedance and capacitance of the second gas path 12 to match those of the first gas path 11, so that flow rate reflective impact of the gas from the first gas path 11 on the second gas path 12 can be reduced, thereby ensuring the measurement precision of the second gas path 12.

Specifically, as shown in FIG. 14, when the switching device 14 of the inhalation branch 10A is in the first mixing mode M1, the one-way valve 165 is turned off, to prevent the gas from the first gas path 11 from entering a gas guide conduit of the second inhalation branch 16. In this case, the first gas path 11 and the second gas path 12 are in communication with the first inhalation branch 15, and a supply gas flows into the first inhalation branch 15 via the first gas path 11 and the second gas path 12 to be provided to the patient 2.

In this implementation, as shown in FIG. 15, when the switching device 14 of the inhalation branch 10A is in the second mixing mode M2, the one-way valve 165 is turned on, and the second flow adjustment device 121 (for example, a solenoid proportional valve) is turned off, so that the mixed gas from the third pressure gas source and the first pressure gas source passes through the one-way valve 165 and the second flow sensor 122 to flow into the second inhalation branch 16 and is provided to the patient 2.

In the inhalation branch 10A in this implementation, the one-way valve 165 is disposed between the third flow adjustment device 161 and the second flow sensor 122, so that the third flow sensor 162 is omitted. In this way, in the similar case in which switching can be performed according to a gas supply source and a mixed gas with a desired oxygen concentration can be provided in time, the costs of the inhalation branch 10A are effectively suppressed from increasing.

In addition, in some examples, the one-way valve 165 may be not disposed. In this case, a gas path may be designed to enable the impedance and capacitance of the second gas path 12 to match those of the first gas path 11. In addition, an algorithm manner and the like may be used to avoid or reduce the influence of flow rate reflective impact of the gas from the first gas path 11 on the second gas path 12, so that the third flow sensor 162 can also be omitted.

Although the present disclosure is described above in detail with reference to the accompanying drawings and the embodiments. However, it may be understood that the foregoing description does not limit the present disclosure in any form. A person skilled in the art may make variations and changes to the present disclosure as required without departing from the essence, spirit, and scope of the present disclosure. All these variations and changes fall within the scope of the present disclosure.

What is claimed is:

1. A ventilator, comprising:
    a first gas path, comprising a first pressurized gas source adaptor and a first flow adjustment device connected in sequence;
    a second gas path, comprising a second pressurized gas source adaptor and a second flow adjustment device connected in sequence;
    a third gas path, comprising a third pressurized gas source adaptor;
    a first inhalation branch configured for delivering inhalation gas to a patient;
    a second inhalation branch configured for delivering inhalation gas to the patient, the second inhalation branch comprising a gas compression device;
    a switching device, configured to operate in a first mixing mode where the first gas path and the second gas path are connected to the first inhalation branch, and in a second mixing mode where the first gas path and the third gas path are connected to the second inhalation branch; and
    an exhalation branch configured for managing exhaled gas of the patient.

2. The ventilator of claim 1, wherein
    the second gas path further comprises a pressure sensor configured for detecting a gas pressure at the second pressurized gas source adaptor; and
    a controller for controlling the switching device based on a measured pressure value of the pressure sensor to enable the switching device to switch between the first mixing mode and the second mixing mode.

3. The ventilator of claim 1, wherein the switching device comprises a pilot valve and a pneumatic three-way valve.

4. The ventilator of claim 1, wherein
    the second inhalation branch further comprises a first mixing cavity, and when the switching device operates in the second mixing mode, the switching device connects the first gas path and the third gas path to the second inhalation branch by the first mixing cavity.

5. The ventilator of claim 1, wherein
    the second inhalation branch further comprises a third flow adjustment device.

6. The ventilator of claim 1, wherein
    the second inhalation branch further comprises a flow sensor.

7. The ventilator of claim 5, wherein
    the third flow adjustment device comprises a voice coil motor.

8. The ventilator of claim 1, wherein.
    the second inhalation branch further comprises a second mixing cavity, and the second mixing cavity is configured for mixing, during inhalation, a gas that is in the second mixing mode and is pressurized by the gas compression device.

9. The ventilator of claim 1, wherein
    a first gas from the first gas path and a second gas from the second gas path are mixed at the first inhalation branch.

10. The ventilator of claim 9, wherein
    the first gas path further comprises a first flow sensor, the second gas path further comprises a second flow sensor; and
    when the switching device operates in the first mixing mode, a difference between a volume of a path from the first flow sensor to a location where the first gas is mixed with the second gas and a volume of a path from the second flow sensor to the location where the second gas is mixed with the first gas does not exceed 40 mL, and a volume of an internal accommodating cavity when the switching device is switched to operate in the first mixing mode does not exceed 30 mL.

11. The ventilator of claim 1, wherein
    the third gas path further comprises a filtering device.

* * * * *